US00PP31072P2

(12) United States Plant Patent
Kordes

(10) Patent No.: US PP31,072 P2
(45) Date of Patent: Nov. 19, 2019

(54) FLORIBUNDA ROSE PLANT NAMED 'KORTEIDROS'

(50) Latin Name: *Rosa hybrida*
Varietal Denomination: KORteidros

(71) Applicant: W. KORDES' SOHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SOHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/998,033

(22) Filed: Jun. 18, 2018

(30) Foreign Application Priority Data

Sep. 20, 2017 (QZ) ..... PBR 20172303

(51) Int. Cl.
*A01H 5/02* (2018.01)
*A01H 6/74* (2018.01)

(52) U.S. Cl.
USPC ..... Plt./142

(58) Field of Classification Search
USPC ..... Plt./142
See application file for complete search history.

(56) References Cited

U.S. PATENT DOCUMENTS

PP19,362 P2 10/2008 Kordes

*Primary Examiner* — Annette H Para
(74) *Attorney, Agent, or Firm* — Buchanan Ingersoll & Rooney PC

(57) ABSTRACT

A new and distinct variety of Floribunda Rose Plant, herein referred to by its cultivar name, 'KORteidros', is provided which forms in abundance on a substantially continuous basis attractive, medium red colored blossoms with a cream reverse. The vegetation is vigorous and the growth habit is very bushy and compact. Attractive ornamental glossy, dark green foliage is formed. The new variety is particularly well suited for providing distinctive ornamentation in the landscape.

2 Drawing Sheets

Figure 1:
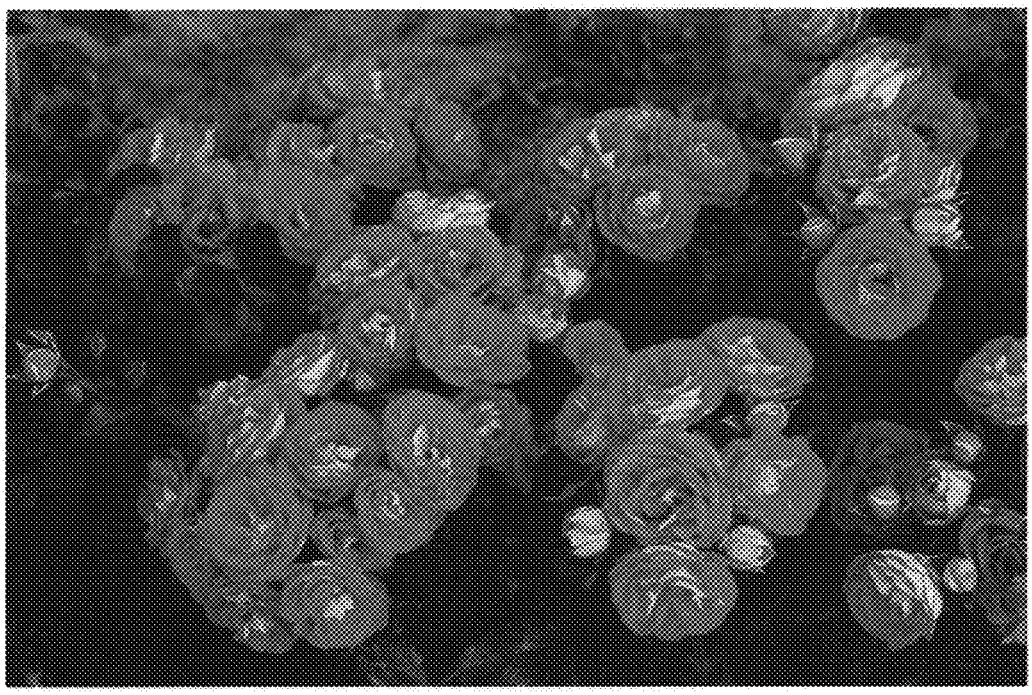

Botanical/commercial classification:
Latin name—*Rosa hybrida.*
Common name—Floribunda Rose Plant.
Varietal denomination: 'KORteidros'.

CROSS-REFERENCE TO RELATED APPLICATIONS

This application claims priority to Plant Breeders' Right Application Number 2017/2303, which was filed at Community Plant Variety Office in the European Union on Sep. 20, 2017, the contents of which are hereby incorporated by reference for all purposes.

SUMMARY OF THE INVENTION

The new variety of *Rosa hybrida* Floribunda Rose Plant of the present invention was created during May 2005 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling from a previous cross between an unnamed seedling (non-patented in the United States) and the 'KORpeligo' variety (non-patented in the United States). The male parent (i.e., pollen parent) of the new variety was the 'KORfloci08' variety (U.S. Plant Pat. No. 19,362).

The parentage can be summarized as follows:

(unnamed seedling x 'KORpeligo') x 'KORfloci08'

The seeds resulting from the above pollination were sown and small plants were obtained which were physically and biologically different from each other. Selective study resulted in the identification of a single plant of the new variety.

It was found that the new Floribunda Rose Plant of the present invention possesses the following combination of characteristics:

(a) abundantly and substantially continuously forms attractive, medium red colored blossoms with a cream reverse,
(b) exhibits a very bushy and compact growth habit,
(c) forms vigorous vegetation, and
(d) forms attractive ornamental glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the (unnamed seedling x 'KORpeligo') variety (i.e., seed parent) exhibits a lower petal count, a less bushy growth habit, and a different flower color compared to the new variety. Additionally, the 'KORfloci08' variety (i.e., pollen parent) exhibits a less rounded flower shape and less disease resistance compared to the new variety and displays orange-red colored flowers, whereas the new variety displays medium red colored flowers with a cream reverse. Moreover, the new variety can be readily distinguished from non-parental related similar varieties. For example, the 'JACzotta' variety (U.S. Plant Pat. No. 12,128) displays less petals and is taller and wider compared to the new variety.

The new variety has been found to undergo asexual propagation in Klein Offenseth-Sparrieshoop, Germany by a number of routes such as budding. Asexual propagation techniques in Germany, such as budding, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORteidros'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately two years of age and was observed at Offenseth-Sparrieshoop, Germany while growing outdoors on understock in July 2017.

FIG. 1—illustrates a specimen of a plant displaying floral buds and flowers at varying points of opening.

Figure 2:
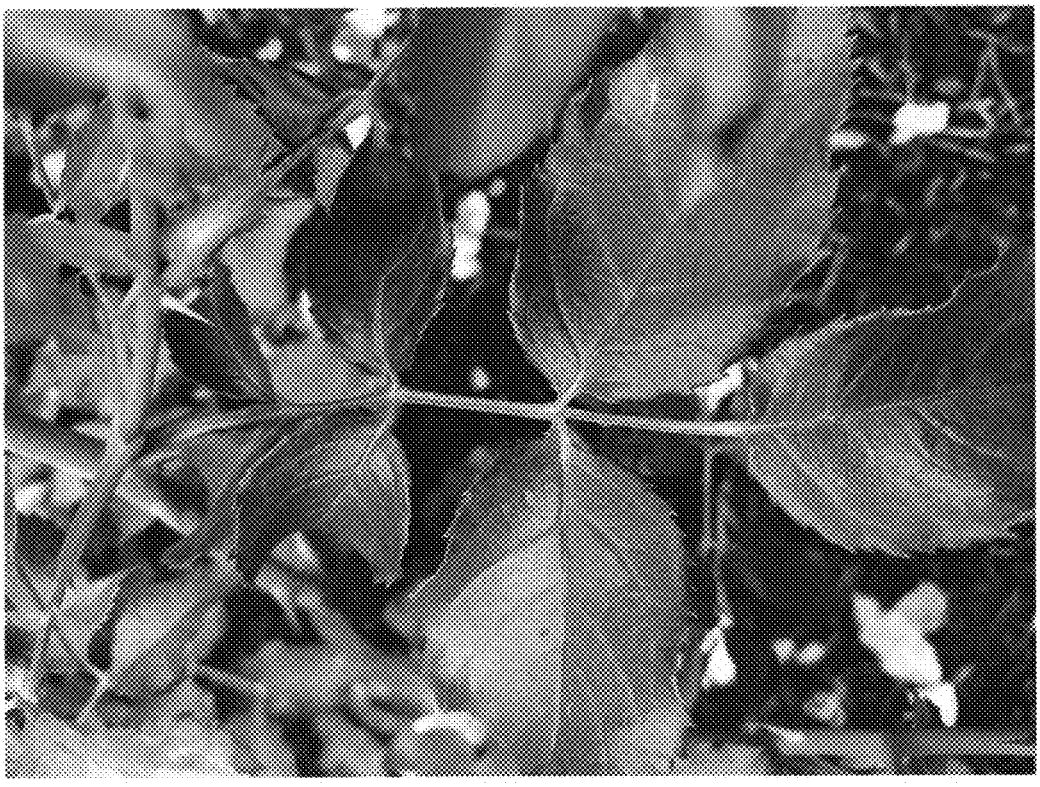

FIG. 2—illustrates a specimen of the foliage—close up view of leaflets.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a three-year-old specimen of the new variety, observed during June, while growing in a field on its own roots at Cochranville, Pa.

Class: Floribunda Rose Plant.

Plant:

*Habit*.—Very bush and compact.

*Height*.—Approximately 50.0 cm on average.

*Width*.—Approximately 50.0 cm on average.

Branches:

*Stem color*.—Young stems: commonly near Yellow-Green Group 144A.

*Stem length*.—Main stem is approximately 50.0 cm on average and secondary stem is approximately 12.0 cm on average.

*Thorns*.—Young thorns: length is approximately 5.0 mm on average, width is approximately 2.0 mm at point of attachment on average, and color is commonly near Yellow-Green Group 152C. Old thorns: length is approximately 1.0 cm on average, width is approximately 6.0 mm at point of attachment on average, and color is commonly near Greyed-Orange Group 166C.

Foliage:

*General appearance*.—Ornamental glossy and dark green colored.

*Young foliage*.—Upper surface color: commonly a blend of near Yellow-Green Group 144A and near Greyed-Orange Group 174A with near Greyed-Orange Group 176A along the margins; and indistinguishable venation. Under surface color: commonly mostly near Greyed-Orange Group 174A with near Yellow-Green Group 144A underneath; and venation of near Greyed-Orange Group 174A.

*Old foliage*.—Upper surface color: commonly near Green Group NN137B with indistinguishable venation. Under surface color: commonly near Green Group 138B with venation of near Greyed-Orange Group 174B only along the midrib.

*Petiole*.—Upper surface: texture is smooth; color is commonly near Green Group 143A. Under surface: texture is smooth; color is commonly near Green Group 143B.

*Rachis*.—Color: upper surface is commonly near Green Group 143A, under surface is commonly near Green Group 143B.

*Stipules*.—Length: approximately 2.5 cm on average. Width: approximately 8.0 mm on average. Margin: entire to erose. Color upper and under surfaces: commonly near Yellow-Green Group 144A.

*Leaf margin*.—Serrate.

*Glossiness of upper side of leaf*.—Very glossy.

Leaflets:

*Number*.—3, 5, and 7.

*Shape*.—Ovate.

*Venation pattern*.—Reticulate.

*Texture*.—Upper surface is smooth; under surface is smooth.

*Terminal leaflet*.—Length is approximately 4.5 cm on average; width is approximately 2.8 cm on average; apex is acute, and base is rounded.

*Lower leaflets*.—Length is approximately 3.5 cm on average and width is approximately 2.5 cm on average.

*7-leaflet leaf*.—Length is approximately 11.0 cm on average and width is approximately 8.0 cm on average.

Inflorescence:

*Number of blossoms per cluster*.—Typically up to 10 blooms in a cluster.

*Peduncle*.—Color: commonly Yellow-Green Group 144A. Diameter: approximately 2.0 mm on average. Length: approximately 3.0 cm on average. Surface texture: sparely covered in short, flexible thorns that measure less than 1.0 mm in length.

*Sepals*.—Number commonly 5. Upper surface color and texture: covered in short pubescence and color is commonly near Yellow-Green Group 144A. Under surface color and texture: puberulent and color is commonly near Yellow-Green Group 144B. Size: length is approximately 1.8 cm on average and width is approximately 9.0 mm on average. Margin: entire with occasional extensions on two or three sepals measuring approximately 3.0 mm in length and approximately 1.0 mm in width.

*Bud*.—Shape: ovoid. Size: length is approximately 2.0 cm on average; width is approximately 1.5 cm on average. Color (when opening): commonly mostly near Red Group 36A with near Red Group 41D near the petal margins and near Yellow Group 13D closest to the sepals.

*Flower*.—Form: double, rounded. Diameter: approximately 3.0 cm on average.

*Fragrance*.—Very light sweet fragrance.

*Petal*.—Number: approximately 37 on average. Drop: good. Length: approximately 2.3 cm on average. Width: approximately 2.0 cm on average. Shape: overall shape is broadly obovate; apex is rounded; and base is rounded to cuneate. Margin: entire. Undulation: moderate. Color with first and fully open: upper surface is commonly near Red Group 45D with basal spot of commonly near White Group 155D; and under surface is commonly near Red Group 36C with basal spot of commonly near White Group N155B.

*Stamen*.—Number: approximately 130 on average. Anthers: number is about 130; color is commonly near is commonly near Greyed- Orange Group 163B; and length is approximately 1.0 mm on average. Filaments: length is approximately 3.0 mm on average and color is commonly near Yellow Group 9C.

*Pistils*.—Arrangement: separate and free. Number: approximately 40. Style: color is commonly near Greyed-Yellow Group 160C; length is approximately 3.0 mm on average. Stigma: color is commonly near Greyed-Yellow Group 160A; diameter is commonly less than 1.0 mm on average.

*Receptacle*.—Achenes stand on the bottom and wall; diameter is approximately 1.3 cm on average, shape is urn shaped to oval, color is commonly near Yellow-Green Group 144A, and surface texture is smooth.

*Pollen*.—None observed.

*Hips/seed*.—None observed.

Development:

*Vegetation*.—Dark green, vigorous, and strong.

*Blooming*.—Abundant and substantially continuous from spring through frost.

*Hardiness*.—Hardy to USDA Zone 5.

*Resistance to disease*.—Very good resistance for mildew.

Plants of the 'KORteidros' variety have not been observed under all possible environmental conditions to date. Accordingly, it is possible that the phenotypic expression may vary somewhat with changes in light intensity and duration, cultural practices, and other environmental conditions.

I claim:

1. A new and distinct Floribunda Rose Plant characterized by the following combination of characteristics:

(a) abundantly and substantially continuously forms attractive, medium red colored blossoms with a cream reverse, (b) exhibits a very bushy and compact growth habit, (c) forms vigorous vegetation, and (d) forms attractive ornamental glossy, dark green foliage; substantially as herein shown and described.

* * * * *